United States Patent [19]

Ollivier et al.

[11] Patent Number: 5,159,112
[45] Date of Patent: Oct. 27, 1992

[54] PROCESS OF THE PRODUCTION OF ALKANESULFONAMIDES

[75] Inventors: Jean Ollivier, Arudy; Michèle Larrouy, Pau, both of France

[73] Assignee: Societe Nationale Elf Aquitaine (Production), France

[21] Appl. No.: 735,118

[22] Filed: Jul. 24, 1991

Related U.S. Application Data

[63] Continuation of Ser. No. 596,638, Oct. 12, 1990, abandoned, which is a continuation of Ser. No. 146,173, Jan. 20, 1988, abandoned.

[30] Foreign Application Priority Data

Jan. 23, 1987 [FR] France ................. 87 00755

[51] Int. Cl.$^5$ ........................................... C07C 311/03
[52] U.S. Cl. ................................................... 564/98
[58] Field of Search ........................................ 564/98

[56] References Cited

U.S. PATENT DOCUMENTS

| | | | |
|---|---|---|---|
| 2,553,093 | 5/1951 | Jacob et al. | 564/98 |
| 3,282,933 | 11/1966 | Nys et al. | 564/98 X |
| 3,755,439 | 8/1973 | Kennedy | 260/556 A |
| 4,377,842 | 6/1943 | Wagner et al. | 564/98 |

FOREIGN PATENT DOCUMENTS 2821193 11/1979 Fed. Rep. of Germany .
694633 7/1953 United Kingdom ................. 564/98

OTHER PUBLICATIONS

Mellan, Industrial Solvents Handbook, 2nd Ed. Noyes Data Corp., 1977, pp. 320–323, 346, 350–352.
Houben-Weyl: "Methoden der Organischen Chemie", Band IX, 1955, Seiten 398–400, Georg Thieme Verlag, Stuttgart.

Primary Examiner—Carolyn Elmore
Attorney, Agent, or Firm—Morgan & Finnegan

[57] ABSTRACT

A process for the preparation of alkanesulfonamides is disclosed. It comprises reacting an alkanesulfonyl chloride with ammonia or with an alkylamine in the presence of a chemically inert liquid diluent. The diluent is first supersaturated with ammonia or with the alkylamine before bringing it into contact with the alkanesulfonyl chloride.

9 Claims, No Drawings

PROCESS OF THE PRODUCTION OF ALKANESULFONAMIDES

This is a continuation of application Ser. No. 596,638, filed Oct. 12, 1990, now abandoned, which is a continuation of application Ser. No. 146,173, filed Jan. 20, 1988, now abandoned.

FIELD OF THE INVENTION

The present invention relates to an improved process for the preparation of alkanesulfonamides and more particularly, methane- and ethane-sulfonamides.

BACKGROUND OF THE INVENTION

The production of methanesulfonamide or its homologues such as ethane- or butane-sulfonamide by reacting methanesulfonyl chloride or its corresponding homologue with ammonia or with a primary or secondary amine is known. Ammonium chloride or an amine hydrochloride, as the case may be, is formed as by-product.

Consequently the accomplishment of this reaction, generally between 10° and 90° C. and usually between 50° and 70° C., in the presence of some liquid diluents such as alcohols, water, optionally chlorinated aliphatic or aromatic hydrocarbons such as methylene chloride and dichloroethane has already been recommended. On the basis of this approach, the French patent application No. 2,010,654 proposes $C_1$-$C_4$ nitroalkanes as diluent.

According to the prior art, the alkanesulfonyl chloride is first dissolved in the diluent and the ammonia or the amine is then introduced into the liquid medium. The above-mentioned French patent application recommends the use of only a slight excess of ammonia or of amine, i.e., only until a slight basicity of the reaction medium is observed.

However, this procedure has severe disadvantages. First of all, its leads to an amide containing various undesirable by-products which are detrimental to the purity of the usable product. For ammonia as the nitrogen-containing reagent, the formation, inter alia, of dialkyldisulfonamide R—$SO_2$—NH—$SO_2$—R, is observed, this involves a wasteful consumption of starting materials, which is unfavorable for achieving a good alkanesulfonamide yield, not to mention additional problems of separation caused by the presence of these by-products.

Additionally, during the separation and recovery of the alkanesulfonamide sought, the reaction mixture must be heated, for example between approximately 50° and 80° C., especially when the actual reaction has been carried out at temperatures below 50° C. The purpose of this heating is to solubilize any alkane-sulfonamide remaining in the form of a precipitate, in the diluent, mixed with the by-product ammonium chloride or amine hydrochloride. This is especially recommended in French patent application No. 2,010,654.

Additionally, the diluents proposed for performing the reaction are unsatisfactory in many respects. Indeed, the nitroalkanes of the above-mentioned publication have inadequate solubility properties at ambient temperature towards alkanesulfonamides. As just mentioned, this makes it necessary to maintain a temperature of at least 50° C. to solubilize the maximum possible amount of alkanesulfonamide. Additionally, it is known that nitroalkanes are solvents which are expensive and difficult to use because of their fairly wide explosibility limits. For example, those for nitromethane are between 7.3 and 63%.

The alcohols, on their part, as they are not sufficiently chemically inert, do not constitute suitable media because they give rise to the formation of dialkyl ehters and alkanesulfonic acid esters as interfering products. Additionally, the by-product, which consists of the amine hydrochloride, is soluble in alcohols. This prevents it from being separated easily, for example, by simply filtering or centrifuging.

Water as diluent gives a quantity of ammonium alkanesulfonate which is not insignificant and which is undesirable.

Finally, the use of optionally chlorinated aliphatic or aromatic hydrocarbons has the disadvantage of maintaining the alkanesulfonamides as well as the by-product salts in an insoluble form. Because of this, the reaction products cannot be separated by simple means of filtration or centrifugation.

DETAILED DESCRIPTION OF THE INVENTION

The object of the present invention is to overcome the many disadvantages of the prior art which have just been described. This is done by making available a process which provides alkanesulfonamides having a high purity and with a high yield, while using chemically inert diluents. Those diluents facilitate separation and recovery of usable product around ambient temperature, by simple means, i.e., without having to raise the temperature of the reaction medium beyond 35°–40° C. during the process.

According to the present process for the preparation of alkanesulfonamides containing 1 to 48 carbon atoms, the corresponding alkanesulfonyl chloride is reacted with ammonia or a primary or secondary alkylamine containing 1 to 12 carbon atoms, in the presence of a substantially anhydrous and chemically inert liquid diluent. The desired alkanesulfonamide is then separated and recovered. The process is characterized in that the diluent is first supersaturated with ammonia or with the primary or secondary alkylamine before bringing it into contact with the alkanesulfonyl chloride. This supersaturation is maintained throughout the reaction period.

Indeed, applicants have found that when alkanesulfonyl chloride is introduced into a liquid medium which has previously been supersaturated with ammonia or with a primary or secondary amine, an alkanesulfonamide of much higher purity than that achieved by the conventional process is obtained. This results in a higher melting point of the desired product. This purity is confirmed by analyses by infrared spectrometry, nuclear magnetic resonance spectrometry, gas chromatography and mass spectrometry.

In the present text, the term "supersaturation" refers to a permanent presence of at least 40 mol %, and preferably from 60 to 80 mol %, relative to the stoichiometry of the reaction, of ammonia or of a primary or secondary amine, in the free state, in the diluent during the process.

According to one embodiment of the process of the present invention, the diluent comprises one or more monoalkoxyalkanes in which the alkoxy is a $C_1$ to $C_3$ alkoxy and the alkane is a $C_1$-$C_4$ alkane.

According to a preferred embodiment of the invention, the diluent comprises one or more dialkoxyalkanes in which the alkoxy is a $C_1$–$C_2$ alkoxy and the alkane is a $C_1$–$C_2$ alkane.

A particularly satisfactory group of diluents of the invention comprises dialkoxyethanes and very particularly dimethoxyethane, which is virtually inert towards the reagents. Thus, the formation of impurities such as by-products in the reaction medium is negligible or at least minimal. Additionally, the by-product salt (ammonium chloride or amine hydrochloride) is essentially insoluble in dimethoxyethane at the reaction temperatures used, preferably between 15° and 30° C. Thus, the dimethoxyethane containing the dissolved alkanesulfonamide, may be recovered by evaporation or distillation and recycled as fresh diluent. Whereas, the entire amount of the sulfonamide is recovered without any by-product.

The reaction temperature is generally between 10° and 40° C. and more particularly from 15° to 35° C., and preferably from 20° to 30° C. and even better at 20° C.

According to the invention, throughout the reaction period, anhydrous ammonia or a primary or secondary amine is introduced into the diluent, at a suitable feed rate. It is advantageous to then incorporate the alkanesulfonyl chloride gradually into the diluent which has previously been supersaturated with the nitrogen-containing reagent.

The reaction time is between 20 and 180 minutes and preferably between 60 and 80 minutes.

It is advisable to carry out the reaction with a molar ratio ammonia or primary or secondary alkylamine: alkanesulfonyl chloride of at least 2, and more particularly, between 3 and 5.

Although the reaction may be carried out at pressures higher than atmospheric pressure, it is convenient and advantageous to work at atmospheric pressure.

It is preferable that water is absent from the reaction medium to avoid undesirable side reactions. Consequently, the reaction medium must be substantially anhydrous, i.e., containing not more than 2% by weight of water.

As the reaction progresses, the main by-product, ammonium chloride or amine hydrochloride, appears in the form of a precipitate. At this stage, the reaction mixture is in the form of a slurry of the crystals of the main by-product in the diluent containing the desired alkanesulfonamide in solution. It is subjected to a liquid-solid separation according to any conventional means, more particularly filtration or centrifugation.

According to a particular feature of the process of the invention, this liquid-solid separation is carried out at a temperature of between 15° and 35° C. and preferably from 20° to 30° C.

It is appropriate to use a gravimetric ratio diluent: alkanesulfonamide from 2:1 to 20:1 and more particularly from 3:1 to 10:1.

Finally, the alkanesulfonamide is separated from the diluent by any conventional means such as, for example, distillation or simple evaporation at atmospheric pressure or under reduced pressure. The alkanesulfonamide is recovered in the form of a powder which can be dried. If desired, the purification of the sulfonamide may be enhanced by redistillation under reduced pressure.

EXAMPLES

The only purpose of the following examples is to illustrate the invention. They must not be regarded as limiting the scope thereof.

EXAMPLE 1

Anhydrous ammonia is passed through 220 ml (191.4 g) of dimethoxyethane (DME) as diluent, until supersaturation. This supersaturation is maintained throughout the period of the neutralization reaction which lasts for 60 minutes. 28 g of methanesulfonyl chloride (MSC) are then introduced in the course of 1 hour using a proportioning pump, while maintaining a rate of supply of gaseous ammonia of 25 l/h, which corresponds to an excess of ammonia of 200 mol % relative to the equimolarity of the neutralization reaction. The reaction temperature is maintained at approximately 20° C. 22.59 g of methane-sulfonamide (MSA) containing 0.17% by weight of chlorine ions and having a melting point of 91.3° C. are thus produced. The yield of this sulphonamide is 97.4% based on the methanesulfonyl chloride used. Only 500 ppm by weight of methyldisulfonamide can be detected from analytical determination. The purity of the product is greater than 98.5%.

The three trials which follow and which are carried out according to the methods of the prior art, are given by way of comparison. It should be noted that in the first two trials, the known diluent was replaced by the DME according to the invention.

1st Trial 28 g of methanesulfonyl chloride (MSC) are dissolved in 220 ml of DME. Gaseous ammonia is then introduced into this mixture until it becomes slightly basic, which corresponds to an excess of $NH_3$ of approximately 10 mol % relative to the stoichiometry of the methanesulfonamide forming reaction. The reaction temperature is approximately 20° C. During the reaction, which lasts for the same length of time as in Example 1, a precipitation of ammonium chloride by-product is observed. The precipitate is filtered off. The $NH_4Cl$ cake is washed with 50 ml of DME. The liquid washing is mixed with the filtrate. The DME in the filtrate is then evaporated under a partial vacuum of 18 mm of Hg in a rotary evaporator and recovered for recycling. 21.95 g of methanesulfonamide having a melting point of 89.5° C. are recovered. The yield of this sulphonamide is 94.7% based on the methanesulfonyl chloride used. Analysis by ion chromatography reveals the presence of 0.2% by weight of chlorine ions. Additionally, chromatographic analysis coupled with mass spectrometry shows the presence of 3% by weight of methanedisulfonamide. The purity of the methanesulphonamide is only 95% as compared with more than 98% for the product obtained according to the invention (Example 1).

2nd Trial

The first trial is repeated, except that 56 g of MSC are neutralized, which amounts to twice the quantity in Trial 1.

44.5 g of methanesulfonamide (melting point 89° C.) having a purity of 94.3% are recovered, with a yield of MSA of 95.8%. Analytical determinations show the presence of 3.8% by weight of methanedisulfonamide.

3rd Trial

The reaction is carried out as in the first trial in Example 1 above, except that the DME is replaced by the same volume of nitroethane.

22.84 g of a yellow-colored and greasy product, melting at 87° C., are thus recovered. The chlorine ion content thereof is 0.25%. The methanesulfonamide yield is only 90 mol %. The purity of the product is only 88%, which is very inadequate.

It is observed, in an unexpected way, that Example 1, when it is carried out according to the process of the present invention, gives methanesulfonamide having a higher purity and with a better yield than those given by known methods.

Additionally, the DME, according to the invention, appears to be of greater efficacy as diluent in comparison with nitroethane, in two ways: a higher solubility of MSA is observed especially at low temperatures (15°–40° C.); whereas at temperatures higher than 50° C.. high concentrations of MSA in nitroethane give rise to the dissolution of $NH_4Cl$ and promote the formation of undesirable by-products.

EXAMPLE 2

The procedure in Example 1 is followed, except that diethoxy ether (DEE) supersaturated with ammonia, is used as diluent instead of DME. The same $NH_3$ excess as in Example 1 is maintained throughout the reaction period.

20.3 g of methanesulfonamide having a melting point of 90° C. are thus produced. The chlorine ion content is 0.111%. The purity of the product is 98.5%, whereas the yield is 87.4%.

EXAMPLE 3

42 g of ethanesulfonyl chloride (ESC) are introduced into 330 ml of DME which has previously been supersaturated with anhydrous ammonia at a gas supply rate of 25 l/h so as to maintain an excess of $NH_3$ of 150 mol % relative to the stoichiometry of the neutralization reaction. The gradual introduction of ESC lasts for 1 h 30 min. The temperature of the reaction medium is maintained at 20° C. The reaction time is 90 minutes.

35 g of ethanesulfonamide (ESA) containing only 0.1% of chlorine ions are thus obtained. The yield of the operation is 98.2% with respect to ESA, and the purity of the product is 98%.

The following two trials are carried out according to the methods of the prior art and are given by way of comparison.

1st Trial

Example 3 is repeated, except that the temperature is set at 50° C. instead of 20° C.

36.1 g of crude product having the following composition are then obtained.
Ethanesulfonamide . . . 87% (31.4 g)
Chlorine ions . . . 0.2%
Ethanedisulfonamide . . . 9.7% by weight (3.5 g)
The product is viscous and very difficult to crystallize. The yield is ESA (in moles) is 88.1%.

2nd Trial

The procedures in the 1st trial following Example 1 is applied, but with ESC and with the same proportions of reagents as those mentioned in Example 3.

The composition of the product recovered is as follows:
Weight of the crude product . . . 35.1 g
Ethanesulfonamide . . . 82% (28.78 g)
Chlorine ions . . . 0.12%
Ethanedisulfonamide . . . 15.6% (5.47 g)
The yield of ESA is 80.75 mol %.

In this case as well, it is observed, in an unexpected way, that the ESA prepared by the process of the invention has a higher purity and a higher yield than those obtained by processes which use temperatures higher than 40° C. and introducing $NH_3$ only after bringing the ESC into contact with the diluent.

EXAMPLE 4

According to the procedure in Example 1, 28 g (0.244M) of MSC are introduced, at 20° C., into 220 ml of DEE (used in Example 2).

20.3 g of MSA having a melting point of 90° C. and a purity of 98.5% are thus produced. The chlorine ion content thereof is 0.111%, whereas the yield is 87.4%.

EXAMPLE 5

Following the procedure in Example 1, but replacing the $NH_3$ by anhydrous gaseous monomethylamine, an excess of 60 mol % of $CH_3NH_2$ relative to the stoichiometry is maintained throughout the reaction period. The rate of supply of $CH_3NH_2$ into the reaction medium which is set at 20° C., is maintained at 23 l/h. 15.65 g of monomethylamine hydrochloride and 24.84 g of N-methylmethanesulfonamide are thus recovered, which amounts to a yield of 93.4% by weight. The chlorine ion content thereof is 1.2%. The overall purity of the product is 97%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A process for preparation of alkanesulfonamides which may contain 1 to 48 carbon atoms, comprising reacting corresponding alkanesulfonyl chloride with ammonia or with a primary or secondary alkylamine containing 1 to 12 carbon atoms, in the presence of a substantially chemically inert liquid diluent, and separating and recovering an alkanesulfonamide, characterized in that the diluent consisting of one or more dialkoxyalkanes in which alkoxy is $C_1$–$C_3$ alkoxy and alkane is a $C_1$–$C_4$ alkane, said diluent is first supersaturated with ammonia or with the primary or secondary alkylamine, before bringing it into contact with the alkanesulfonyl chloride, and in that this supersaturation is maintained throughout the reaction.

2. The process according to claim 1, wherein the supersaturation corresponds to between 60 to 80 mol % of ammonia or of primary or secondary amine, in the free state, in the diluent, relative to the stoichiometry of the reaction.

3. The process according to claim 1, wherein reaction temperature is from 15° to 35° C.

4. The process according to claim 3, wherein the reaction temperature is from 20° to 30° C.

5. The process according to claim 1, wherein the separation and the recovery of the alkanesulfonamide are carried out at a temperature between 15° and 35° C.

6. The process according to claim 5, wherein the separation and the recovery of the alkanesulfonamide are carried out at a temperature between 20° to 30° C.

7. The process according to claim 1, wherein the gravimetric ratio diluent:alkanesulfonamide is from 2:1 to 20:1.

8. The process according to claim 7, wherein the gravimetric ratio diluent:alkanesulfonamide is from 3:1 to 10:1.

9. The process according to claim 1, wherein the diluent is dimethoxyethane.

* * * * *